United States Patent
Nitta

(10) Patent No.: US 9,821,136 B2
(45) Date of Patent: Nov. 21, 2017

(54) OPENING AND CLOSING DEVICE AND RESPIRATORY ASSISTANCE DEVICE

(71) Applicant: Metran Co., Ltd., Kawaguchi-shi, Saitama (JP)

(72) Inventor: Kazufuku Nitta, Kawaguchi (JP)

(73) Assignee: METRAN CO., LTD., Kawaguchi-shi, Saitama (JP)

(*) Notice: Subject to any disclaimer, the term of this patent is extended or adjusted under 35 U.S.C. 154(b) by 357 days.

(21) Appl. No.: 14/391,872

(22) PCT Filed: Apr. 15, 2013

(86) PCT No.: PCT/JP2013/061191
§ 371 (c)(1),
(2) Date: Oct. 10, 2014

(87) PCT Pub. No.: WO2013/157517
PCT Pub. Date: Oct. 24, 2013

(65) Prior Publication Data
US 2015/0101610 A1    Apr. 16, 2015

(30) Foreign Application Priority Data

Apr. 16, 2012   (JP) ................ 2012-092792

(51) Int. Cl.
*A61M 16/20*     (2006.01)
*F04D 33/00*     (2006.01)
(Continued)

(52) U.S. Cl.
CPC ...... *A61M 16/205* (2014.02); *A61M 16/0066* (2013.01); *A61M 16/06* (2013.01);
(Continued)

(58) Field of Classification Search
CPC .. A61M 16/205; A61M 16/202; A61M 16/06; A61M 16/20; A61M 16/0066; F04D 33/00; F16K 31/006
See application file for complete search history.

(56) References Cited

U.S. PATENT DOCUMENTS 4,811,730 A    3/1989   Milano
5,315,989 A    5/1994   Tobia
(Continued)

FOREIGN PATENT DOCUMENTS

DE   10 2007 027 900 A1   12/2008
EP       1 655 052 A2      5/2006
(Continued)

OTHER PUBLICATIONS

Supplementary European Search Report issued in Appln. No. EP 13779001.0 dated Jun. 24, 2015 (6 pages).
(Continued)

*Primary Examiner* — (Jackie) Tan-Uyen T Ho
*Assistant Examiner* — Jonathan Paciorek
(74) *Attorney, Agent, or Firm* — Flynn, Thiel, Boutell & Tanis, P.C.

(57) ABSTRACT

A respiratory assistance device 10 includes: a mask 13 having an expiratory hole 13a; an expiratory valve 15 provided in the mask 13, for opening and closing the expiratory hole 13a; and a control unit 17 for performing overall control on the entire device. The mask 13 and the expiratory valve 15 together form an opening and closing device. The expiratory valve 15 is deformable by deformation of a piezo element 15a. The expiratory valve 15 is disposed on an inner surface 13f so that a deformation direction thereof, i.e., a thickness direction thereof, extends (Continued)

along the inner surface 13f of the mask 13 and a side surface 15m slides along the inner surface 13f by the deformation thereof.

11 Claims, 16 Drawing Sheets

(51) Int. Cl.
    *A61M 16/00*     (2006.01)
    *F16K 31/00*     (2006.01)
    *A61M 16/06*     (2006.01)

(52) U.S. Cl.
    CPC .......... *A61M 16/20* (2013.01); *A61M 16/202* (2014.02); *F04D 33/00* (2013.01); *F16K 31/006* (2013.01); *A61M 16/0012* (2014.02); *A61M 16/0051* (2013.01); *A61M 2016/0027* (2013.01); *A61M 2016/0039* (2013.01); *A61M 2205/0266* (2013.01); *A61M 2205/0294* (2013.01); *A61M 2205/502* (2013.01); *A61M 2205/52* (2013.01); *F04C 2270/041* (2013.01)

(56) References Cited

U.S. PATENT DOCUMENTS

| | | | |
|---|---|---|---|
| 6,106,245 A | 8/2000 | Cabuz | |
| 6,179,586 B1 | 1/2001 | Herb et al. | |
| 6,923,181 B2 * | 8/2005 | Tuck | A61M 16/20 128/205.24 |
| 8,678,787 B2 | 3/2014 | Hirata et al. | |
| 2005/0072428 A1 * | 4/2005 | Ho | A61M 16/06 128/205.25 |
| 2005/0126573 A1 * | 6/2005 | Jaffre | A61M 16/08 128/207.12 |
| 2007/0062536 A1 * | 3/2007 | McAuley | A61M 16/06 128/206.21 |
| 2008/0276937 A1 * | 11/2008 | Davidson | A61M 16/06 128/204.18 |
| 2009/0050137 A1 | 2/2009 | Wissink et al. | |
| 2009/0232682 A1 | 9/2009 | Hirata et al. | |
| 2009/0232683 A1 | 9/2009 | Hirata et al. | |

FOREIGN PATENT DOCUMENTS

| | | |
|---|---|---|
| GB | 2 404 866 A | 2/2005 |
| JP | 2-131765 A | 5/1990 |
| JP | 2-131773 A | 5/1990 |
| JP | 2-131774 A | 5/1990 |
| JP | 3-136665 A | 6/1991 |
| JP | 5-245204 A | 9/1993 |
| JP | 2006-214493 A | 8/2006 |
| WO | WO 2008/069266 A1 | 6/2008 |
| WO | WO 2011/144541 A1 | 11/2011 |

OTHER PUBLICATIONS

European Search Report of PCT/JP2013/061191 dated Feb. 23, 2015 (6 pages).
International Search Report issued in PCT/JP2013/061191 with English translation dated Jul. 16, 2013 (4 pages).

* cited by examiner (A)

(B)

(A)

(B)

(A)

(B)

United States Patent US 9,821,136 B2

OPENING AND CLOSING DEVICE AND RESPIRATORY ASSISTANCE DEVICE

TECHNICAL FIELD

The present invention relates to an opening and closing device and a respiratory assistance device.

BACKGROUND ART

Respiratory assistance devices such as artificial respirators are used in medical practice. A typical respiratory assistance device includes an oxygen supply source such as an oxygen tank, an inspiratory pipe connected to the supply source, a mask attached to a tip of the inspiratory pipe, an expiratory pipe branched from the inspiratory pipe, an expiratory valve fixed to a tip of the expiratory pipe, etc. (for example, Japanese Patent Application Laid-Open Nos. Hei. 02-131765, Hei. 02-131773, Hei. 02-131774, and Hei. 05-245204).

Various methods such as a controlled ventilation (Controlled Ventilation) method used for a patient in the absence of spontaneous breathing (a patient under general anesthesia, during cardiopulmonary resuscitation, or in a critical condition) and an assisted ventilation (Assisted Ventilation) method in which a positive pressure (Positive Pressure) is created in an air passage in synchronization with the spontaneous breathing of a patient are employed for such respiratory assistance devices.

In a respiratory assistance device employing any of these methods, oxygen sent out from the oxygen tank is supplied to lungs as inspiratory air via the inspiratory pipe. The oxygen supplied to the lungs is then exhaled by the lungs as expiratory air. If the expiratory air is discharged into the expiratory pipe, a pressure in the expiratory pipe is increased. A control unit then receives a sensing signal from a pressure sensor having detected the pressure increase in the expiratory pipe and opens the expiratory valve. In this manner, the expiratory air is emitted to the outside from the expiratory pipe.

SUMMARY OF INVENTION

Technical Problem

A diaphragm valve has been known as an expiratory valve employed in such a respiratory assistance device. The diaphragm valve includes: a valve seat formed along a circumference of an opening of a hole through which the expiratory air passes (hereinafter referred to as an expiratory hole); and a valve element movable between a position supported by the valve seat and blocking the expiratory hole (blocking position) and a position away from the valve seat and opening the expiratory hole (opening position).

The valve element of this diaphragm valve is required to have a rigidity just enough to resist a pressure from the expiratory hole in order to maintain the blocking position. As means for enhancing the rigidity of the valve element, changing the forming material thereof, reviewing the shape thereof, increasing the size of the valve element itself, and the like, can be considered.

However, if the forming material or shape of the valve element is changed, the procurement cost or processing cost thereof is thereby increased. Moreover, if the size of the valve element itself is increased, the downsizing of the diaphragm valve becomes difficult to achieve. These problems are not limited to the expiratory valve employed in the respiratory assistance device but common to the diaphragm valve.

The present invention has been made in view of the aforementioned problems. It is an object of the present invention to provide an opening and closing device having a rigidity enough to resist a pressure from the hole and capable of being manufactured inexpensively and downsized easily, and a respiratory assistance device including the opening and closing device.

Solution to Problem

As a result of intensive research made by the present inventor, the aforementioned object is achieved by the following means.

An opening and closing device includes: a separating member having a separating surface with a hole through which a fluid passes when opened; and an opening and closing mechanism having a deformable member deformable in a plane direction of the separating surface, wherein the opening and closing mechanism can be transitioned by deformation of the deformable member between a first state and a second state in which opening amounts of the hole are different from each other.

Preferably, the deformable member is formed in a shape of a plate deformable in a thickness direction thereof, and the deformable member extends from the separating surface so that a direction of the deformation coincides with the plane direction of the separating surface. Moreover, the hole is preferably formed in a slit shape and the deformable member preferably covers the hole with a side surface thereof.

Preferably, the opening and closing mechanism includes a cover provided at a free end side of the deformable member and covers the hole by moving the cover. Moreover, said hole includes a first hole and a second hole and the first hole and the second hole are preferably opened in the separating surface, and the opening and closing mechanism preferably can be transitioned by deforming the common deformable member between a state in which the first hole is blocked and the second hole is opened and a state in which the second hole is blocked and the first hole is opened.

Preferably, the deformable member is a piezoelectric element, and the opening and closing device includes a controller for controlling deformation of the piezoelectric element. Moreover, a biasing mechanism for biasing the opening and closing mechanism toward the separating surface is preferably provided.

A respiratory assistance device includes the above-described opening and closing device, and the separating member is formed by: a mask for covering a nose or a mouth; and a communicating pipe which communicates with a space formed inside the mask in a worn state.

The hole is preferably formed in the mask or the communicating pipe. Moreover, the hole preferably forms an expiratory pathway through which expiratory air is exhaled from the nose or the mouth passes.

A respiratory assistance device includes: the above-described opening and closing device; a flow passage through which an expiratory or inspiratory gas passes; an inspiratory nozzle disposed in the flow passage, for jetting an acceleration gas in an inspiratory direction; an expiratory nozzle disposed in the flow passage closer to an expiratory direction side than the inspiratory nozzle, for jetting an acceleration gas in the expiratory direction; a pump unit for supplying the acceleration gas to the inspiratory nozzle and the expiratory nozzle; an inspiratory Venturi wall extending from the inspiratory nozzle toward the inspiratory direction in the flow passage so as to spread out the acceleration gas emitted from the inspiratory nozzle in order to set the inspiratory direction side from the inspiratory nozzle at a negative pressure; and an expiratory Venturi wall extending from the expiratory nozzle toward the expiratory direction in the flow passage so as to spread out the acceleration gas emitted from the expiratory nozzle in order to set the expiratory direction side from the expiratory nozzle at a negative pressure, wherein the opening and closing device can be transitioned between a state in which one of the inspiratory nozzle and the expiratory nozzle is blocked and a state in which the other one of them is blocked.

Advantageous Effects of Invention

The above-described opening and closing device has a rigidity sufficient to resist a pressure from the hole and can be manufactured inexpensively and downsized easily. Such an opening and closing device is suitable for use also as an opening and closing device (for example, an expiratory valve) in a respiratory assistance device.

DESCRIPTION OF EMBODIMENTS

Embodiments of the present invention will now be described below with reference to the accompanying drawings.

Figure 1:
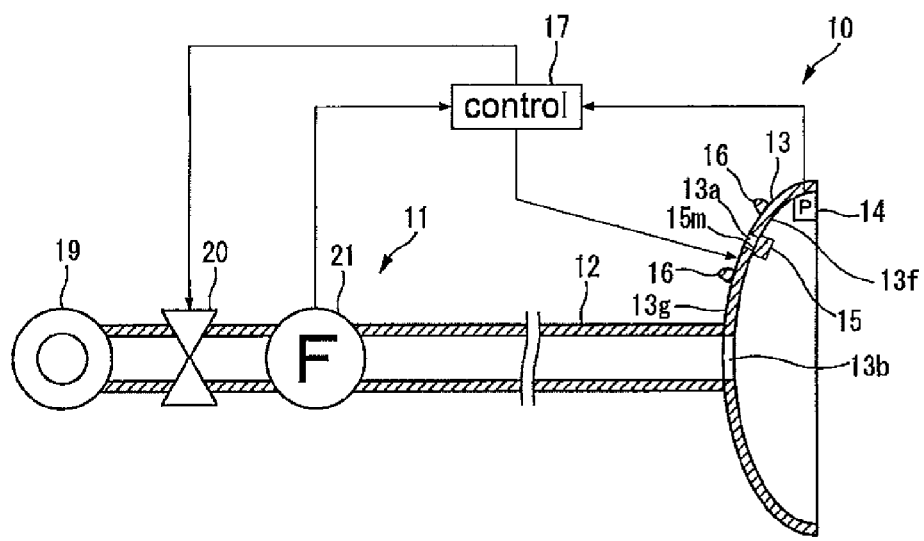
FIG. 1 is a schematic view illustrating a configuration of a respiratory assistance device according to a first embodiment of the present invention.

FIG. 1 illustrates, as an example, a configuration of a respiratory assistance device 10 for medical use according to the first embodiment of the present invention. The respiratory assistance device 10 includes: a supply source 11 for sending out an inspiratory gas; an inspiratory pipe 12 with its base end being connected to the supply source 11; a mask 13 attached to a tip of the inspiratory pipe 12 and having an expiratory hole 13a; an air gauge 14 for measuring a gas pressure inside the mask 13; an expiratory valve 15 provided in the mask 13 and serving as an opening and closing mechanism for the expiratory hole 13a; a plurality of safety members 16 provided around the expiratory hole 13a so as to protrude toward the outer side of an expiratory pathway; and a control unit 17 for performing overall control on the entire device. The mask 13 and the expiratory valve 15 together form an opening and closing device.

The mask 13 is a wearing device that covers a mouth and a nose. The mask 13 serves to separate the mouth and the nose from the ambient air (separating member). The mask 13 is provided with an inspiratory hole 13b. The inspiratory pipe 12 and the mask 13 communicate with each other via the inspiratory hole 13b. An inspiratory pathway is formed by the inspiratory pipe 12, the inspiratory hole 13b, and the mask 13. The expiratory pathway is formed by the mask 13 and the expiratory hole 13a. Note that the mask 13 may be a wearing device that covers either the mouth or the nose.

The supply source 11 includes: a gas tank 19 that retains a gas such as air or oxygen in a compressed state; a regulating valve 20 for regulating a flow rate of the gas sent out from the gas tank 19; and a flowmeter 21 for measuring the flow rate of the gas regulated by the regulating valve 20. The regulating valve 20 is controlled on the basis of sensing data (measured results, sensing signals) from the air gauge 14 and from the flowmeter 21. While the regulating valve 20 is not limited to a particular type, an electric valve, an electromagnetic valve with a high response speed, or the like, can be employed. The flowmeter 21 outputs the sensing data to the control unit 17.

The inspiratory pipe 12 is formed by a bellows tube made of a resin. The inspiratory pipe 12 and the mask 13 worn by a patient together form a space and serve as a pathway for the gas sent out from the supply source 11. A gas pressure inside the inspiratory pipe 12 coincides with a gas pressure inside the mask 13 worn by the patient in a steady state. The air gauge 14 outputs the sensing data to the control unit 17.

As shown in FIGS. 2A to 2D, the expiratory valve 15 emits the gas inside the mask 13 to the outside of the mask 13 by opening and closing the expiratory hole 13a formed in a slit shape and functions as a check valve for preventing a back-flow thereof. The plate-shaped expiratory valve 15 is a valve having a monomorph (unimorph) structure in which a piezo element (piezoelectric element) 15a to be displaced according to an amount of voltage applied is layered on a metal plate 15b and having a cantilever structure. The respiratory assistance device 10 further includes a fixing member 22 for fixing one end of the expiratory valve 15 to the mask 13. The fixing member 22 is provided so as to extend from an inner surface 13f of the mask 13. The one end of the expiratory valve 15 is fixed to the mask 13 by the fixing member 22 with a position erecting from the inner surface 13f. Note that the fixing member 22 is preferably provided with a fixing groove into which the one end of the expiratory valve 15 can be fitted. A cantilever length of the expiratory valve 15 is preferably about 30 mm or more and about 40 mm or less. A displacement stroke of the expiratory valve 15 is preferably 2 mm or more and 3 mm or less. Note that the piezo element may have a both-end supported structure.

The piezo element 15a is deformable between an extended state (see FIGS. 2A and 2B) and a bent state (see FIGS. 2C and 2D) by turning ON and OFF the voltage application thereto. When the piezo element 15a is in the extended state, a side surface 15m of the expiratory valve 15 is in a state in which the expiratory hole 13a is opened. When the piezo element 15a is in the bent state, on the other hand, the side surface 15m of the expiratory valve 15 is in a state in which the expiratory hole 13a is blocked. In this manner, the expiratory valve 15 becomes deformable as a result of the deformation of the piezo element 15a. Moreover, the expiratory valve 15 is provided on the inner surface 13f so that a deformation direction thereof, i.e., a thickness direction thereof, coincides with the plane direction of the inner surface 13f of the mask 13. Moreover, it is preferable that the expiratory valve 15 be provided on the inner surface 13f so that the side surface 15m slides along the inner surface 13f by the deformation of the expiratory valve 15. The inner surface 13f may be a flat surface or a curved surface. Thus, the expiratory valve 15 can be transitioned by the deformation of the piezo element 15a between the state in which the expiratory hole 13a formed in the mask 13 is opened (see FIGS. 2A and 2B) and the state in which by the side surface 15m of the expiratory valve 15, the expiratory hole 13a is blocked by the side surface 15m (see FIGS. 2C and 2D).

The piezo element 15a may be in the bent state when a voltage is being applied thereto and in the extended state when no voltage is being applied thereto as shown in FIGS. 2A to 2D. Or alternatively, the piezo element 15a may be in the extended state when a voltage is being applied thereto and in the bent state when no voltage is being applied thereto.

Although the expiratory valve 15 with the monomorph structure is introduced here, it is apparent that a bimorph structure in which two piezo elements are attached together can be employed instead.

Referring back to FIG. 1, if the expiratory hole 13a is covered by an object outside the mask 13, the expiratory pathway cannot be secured by the actuation of the expiratory valve 15. It is therefore preferable that the safety members 16 be provided in the mask 13. The safety members 16 are formed so as to protrude from an outer surface 13g of the mask 13 and arranged so as to be dotted near the expiratory hole 13a. Consequently, a gap can be formed between an aperture plane of the expiratory hole 13a on the outer surface 13g side and the object covering the expiratory hole 13a. Thus, the expiratory pathway can be secured by the actuation of the expiratory valve 15.

Figure 3:
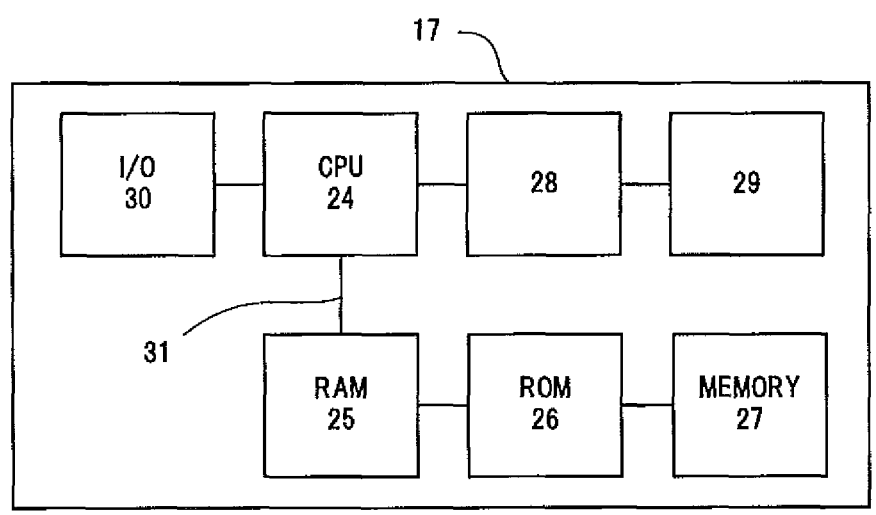
FIG. 3 is a block diagram illustrating a hardware configuration of a control unit.

As shown in FIG. 3, the control unit 17 includes a CPU 24, a first storage medium 25, a second storage medium 26, a third storage medium 27, an input device 28, a display device 29, an input and output interface 30, and a bus 31.

The CPU 24 is what is called a central processing unit and executes various programs to realize various functions of the control unit 17. The first storage medium 25 is what is called a RAM (Random Access Memory) and used as a work area for the CPU 24. The second storage medium 26 is what is called a ROM (Read Only Memory) and stores a basic operating system executed by the CPU 24. The third storage medium 27 is configured by a hard disk device incorporating a magnetic disk, a disk device accommodating a CD, a DVD, or a BD, a non-volatile semiconductor flash memory device, and the like. The third storage medium 27 saves various programs executed by the CPU 24.

The input device 28 is an input key, a keyboard, or a mouse and inputs a variety of information. The display device 29 is a display and displays various operating states. A power supply for operating the expiratory valve 15 and control signals are inputted to and outputted from the input and output interface 30. Furthermore, the input and output interface 30 also obtains data such as a program from an external personal computer. The bus 31 serves as a line for integrally connecting the CPU 24, the first storage medium 25, the second storage medium 26, the third storage medium 27, the input device 28, the display device 29, the input and output interface 30, and the like to achieve communication among them.

Figure 4:
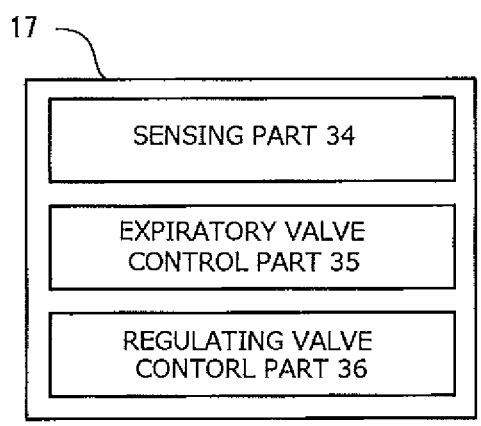
FIG. 4 is a block diagram illustrating a functional configuration of the control unit.

FIG. 4 shows a functional configuration obtained when a control program stored in the control unit 17 is executed by the CPU 24. The control unit 17 includes: a sensing part 34; an expiratory valve control part 35; and a regulating valve control part 36, as the functional configuration. The sensing part 34 constantly obtains the sensing data from the air gauge and transmits such data to the expiratory valve control part 35. Furthermore, the sensing part 34 constantly obtains the sensing data from the air gauge 14 and the flowmeter 21 and transmits such data to the regulating valve control part 36. The expiratory valve control part 35 refers to the sensing data from the sensing part 34 and controls a control signal to the expiratory valve 15 so as to approximate a target opening amount. The regulating valve control part 36 refers to the sensing data from the sensing part 34 and controls a control signal to the regulating valve 20 so as to approximate a target flow rate value.

Figure 5:
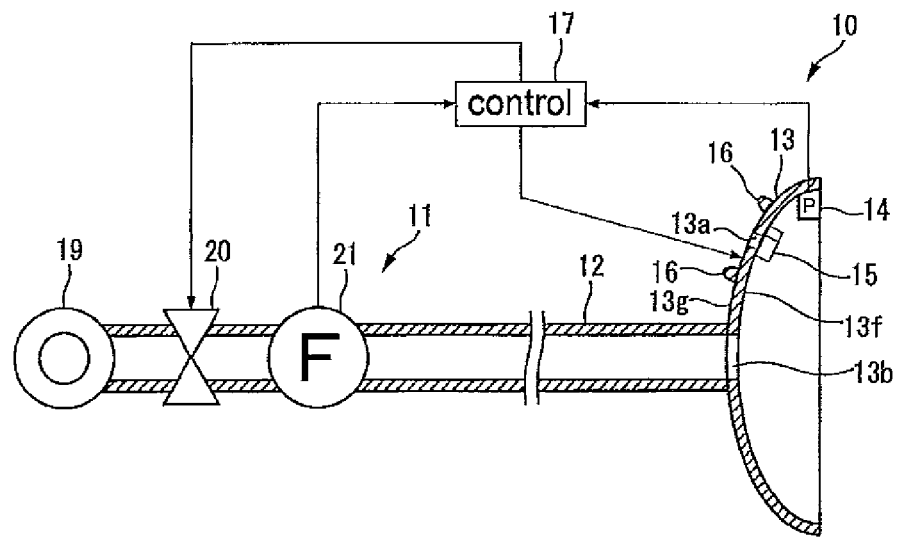
FIG. 5 shows schematic views illustrating a control example of the respiratory assistance device wherein (A) shows a case when a user performs expiration and (B) shows a case when the user performs inspiration.
Figure 5:
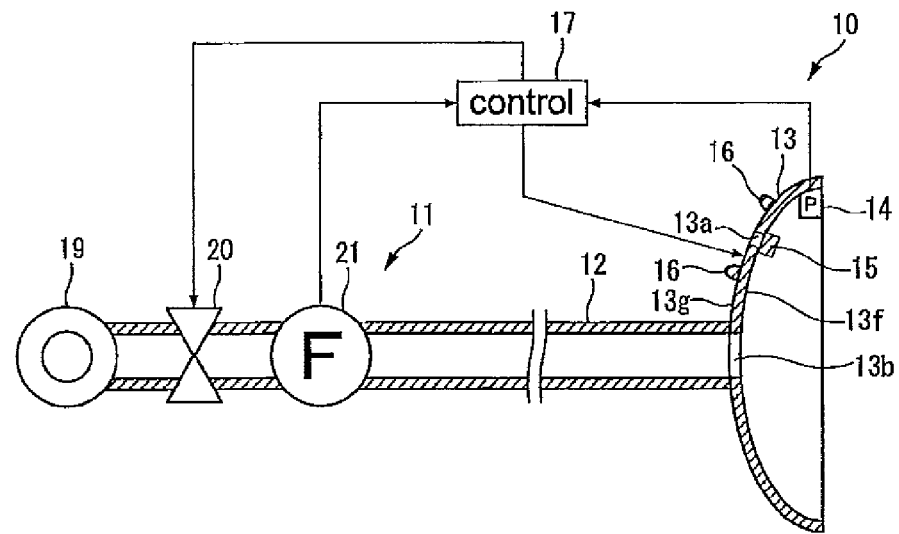

Control examples for the respiratory assistance device 10 will be described next with reference to FIG. 5(A) and FIG. 5(B).

First of all, if expiratory air is exhaled from a mouth or nose wearing the mask 13, the pressure inside the mask 13 is increased. If the pressure inside the mask 13 is increased, the increased value is sensed by the air gauge 14. The sensing data is outputted to the control unit 17. The control unit 17 controls the expiratory valve 15 on the basis of the sensing data. More specifically, the control unit 17 operates the expiratory valve 15 so as to open the expiratory hole 13a as shown in FIG. 5(A). The expiratory air is emitted to the outside of the mask 13 through the expiratory hole 13a.

Emitting the expiratory air to the outside of the mask 13 causes the pressure inside the mask 13 to decrease. If the pressure inside the mask 13 is decreased, the decreased value is sensed by the air gauge 14. The sensing data is outputted to the control unit 17. The control unit 17 controls the expiratory valve 15 on the basis of the sensing data. More specifically, the control unit 17 operates the expiratory valve 15 so as to block the expiratory hole 13a. Consequently, a closed space is formed inside the mask 13, thereby allowing for an inspiratory operation.

Subsequently, when inspiration is performed by the mouth or nose wearing the mask 13, the pressure inside the mask 13 is decreased. If the pressure inside the mask 13 is decreased, the decreased value is sensed by the air gauge 14. The sensing data is outputted to the control unit 17. The control unit 17 controls the supply source 11 on the basis of the sensing data. More specifically, the control unit 17 opens the regulating valve 20 so as to send out the gas from the gas tank 19 as the inspiratory air as shown in FIG. 5(B). Thereafter, the pressure inside the mask 13 is increased. If the pressure inside the mask 13 is increased, the increased value is sensed by the air gauge 14. The sensing data is outputted to the control unit 17. The control unit 17 controls the supply source 11 on the basis of the sensing data. More specifically, the control unit 17 closes the regulating valve 20 so as to stop the sending out of the gas from the gas tank 19 as the inspiratory air. Thereafter, the expiratory operation and the inspiratory operation are repeated in the same manner.

Here, if the deformation direction of the piezo element 15a coincides with a direction away from the inner surface 13f or closer to the inner surface 13f, the deformation direction of the piezo element 15a is substantially parallel to the direction of a force generated by a pressure difference between the inside and outside of the mask 13. Thus, the piezo element 15a is easily deformed by the force generated by the pressure difference between the inside and outside of the mask 13. In the above-described respiratory assistance device 10, on the other hand, the expiratory valve 15 is disposed so that the deformation direction of the piezo element 15a coincides with a direction along the inner surface 13f. Therefore, the deformation direction of the piezo element 15a is substantially perpendicular to the direction of the force generated by the pressure difference between the inside and outside of the mask 13. Consequently, the piezo element 15a is hardly deformed by the force generated by the pressure difference between the inside and outside of the mask 13. In this manner, the expiratory valve 15 is rigid enough to resist the pressure from the expiratory hole 13a. Moreover, since the piezo element can be used as the expiratory valve 15 itself, an increase in procurement cost or processing cost can be avoided.

As described above, the opening and closing device formed by the mask 13 and the expiratory valve 15 is rigid enough to resist the pressure from the hole and can be manufactured inexpensively and downsized easily. Furthermore, due to its simple configuration, the opening and closing device can easily obtain a high reliability.

Moreover, the expiratory valve 15 is disposed so that the deformation direction of the piezo element 15a coincides with the direction along the inner surface 13f. Therefore, as compared with the case where the deformation direction of the piezo element 15a coincides with the direction away from the inner surface 13f or closer to the inner surface 13f, a fully-opened state of the expiratory hole 13a can be easily obtained with a smaller deformation amount of the piezo element 15a.

Moreover, since the piezo element 15a, capable of easily adjusting the deformation amount thereof by an applied voltage value, is used, the opening percentage of the expiratory hole 13a can be easily adjusted. Consequently, the discharge amount of the expiratory air can be adjusted. Therefore, the flow rate of the expiratory air emitted from the expiratory valve 15 can be prevented from changing abruptly. In other words, the gas pressure inside the mask 13 can be prevented from changing abruptly, thereby easing a load on the patient.

Furthermore, the expiratory valve 15 is configured to include the piezo element 15a. Thus, as compared with a case where an electromagnetic valve is employed as the expiratory valve, the expiratory valve 15 has a longer lifetime and is more durable.

Thus, the application of the present invention allows for use as a home artificial respirator by a patient suffering from sleep apnea syndrome or the like.

Moreover, the expiratory valve 15 is in the state in which the expiratory hole 13a is opened when no voltage is being applied to the piezo element 15a. Therefore, even when the expiratory valve 15 stops its operation due to a failure or the like, the expiratory valve 15 is forced to be in the state in which the expiratory hole 13a is opened. Thus, the expiratory pathway can be secured.

Also, since the expiratory valve 15 is provided in the mask 13, the responsiveness of the expiratory valve 15 to the expiratory operation is high. Thus, a load on the patient is small.

Furthermore, since the expiratory valve 15 is provided inside the mask 13, the expiratory valve 15 can be prevented from interfering with an object outside the mask 13. Note that the expiratory valve 15 may be provided on the outer surface of the mask 13.

Figure 6:
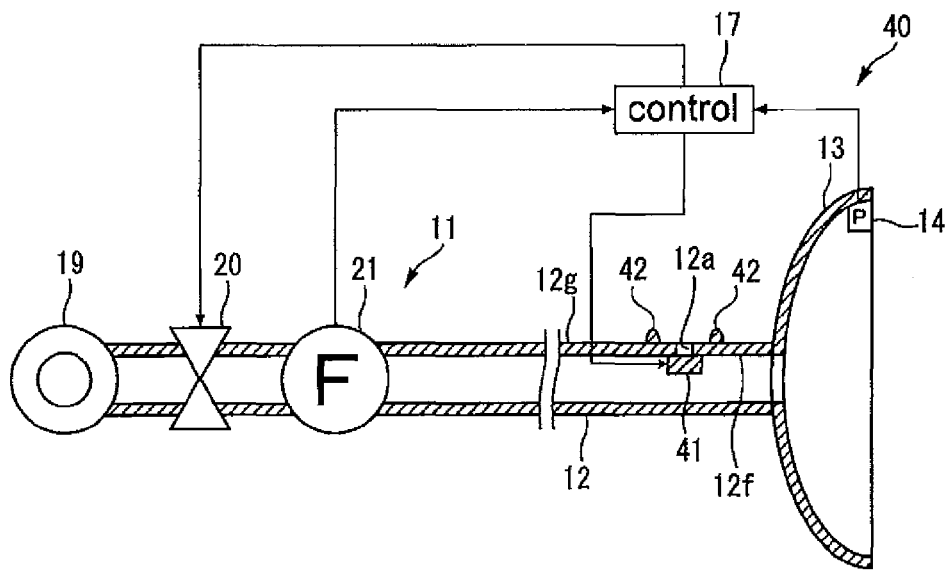
FIG. 6 is a schematic view illustrating a configuration of a respiratory assistance device according to a second embodiment of the present invention.

FIG. 6 illustrates, as an example, a configuration of a respiratory assistance device 40 according to the second embodiment. The first embodiment and the second embodiment have many identical or similar portions. The description of such portions will be therefore omitted when appropriate and points different from those in the first embodiment will be described mainly. Also, with regard to the third and following embodiments to be described later, descriptions common to the other embodiments will be omitted when appropriate and points different from those in the other embodiments will be described mainly.

In the respiratory assistance device 40, a vent hole 12a is formed in the inspiratory pipe 12 instead of forming the expiratory hole 13a (see FIG. 1) in the mask 13. Also, instead of providing the expiratory valve 15 and the plurality of safety members 16 in the mask 13, an expiratory valve 41 and a plurality of safety members 42 are provided in the inspiratory pipe 12 according to the respiratory assistance device 40. Thus, the inspiratory pipe 12 functions also as the expiratory pathway.

The expiratory valve 41, having a configuration similar to the expiratory valve 15 shown in FIGS. 2A to 2D, is provided on an inner surface 12*f* such that a deformation direction thereof, i.e., a thickness direction thereof, extends along the inner surface 12*f* of the inspiratory pipe 12 and a side surface thereof slides along the inner surface 12*f* by the deformation thereof. Thus, the expiratory valve 15 can be transitioned by the deformation of the piezo element between a state in which the vent hole 12*a* is opened and a state in which the vent hole 12*a* is closed. Moreover, the safety members 42 are formed so as to protrude from an outer surface 12*g* of the inspiratory pipe 12 and arranged so as to be dotted near the vent hole 12*a*.

It is preferable that the expiratory valve 41 be provided at a position as close as possible to the mask 13 within a range not causing a slow responsiveness to the expiratory operation. Specifically, the expiratory valve 41 is provided preferably at a position where a length from the mask 13 in the inspiratory pipe 12 is within 300 mm, and more preferably at a position within 100 mm. In other words, the expiratory valve 41 is provided preferably at a position where a distance of the expiratory pathway from an entrance into a body such as a mouth is within 310 mm, and more preferably at a position within 110 mm.

Figure 7:
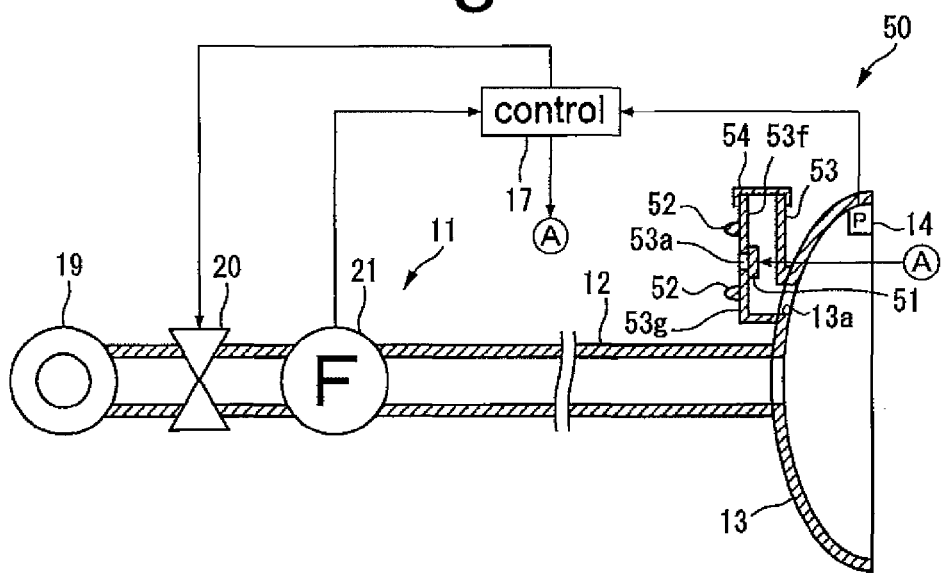
FIG. 7 is a schematic view illustrating a configuration of a respiratory assistance device according to a third embodiment of the present invention.

FIG. 7 illustrates, as an example, a configuration of a respiratory assistance device 50 according to the third embodiment. In the respiratory assistance device 50, an expiratory valve 51 and a plurality of safety members 52 are provided in the mask 13 via an exhaust pipe 53 instead of providing the expiratory valve 15 and the plurality of safety members 16 directly on the mask 13. More specifically, the exhaust pipe 53 is provided on the mask 13 so that a base end thereof covers the expiratory hole 13*a*. A tip of the exhaust pipe 53 is closed by a cap 54. A vent hole 53*a* is formed in a middle portion of the exhaust pipe 53. Thus, the exhaust pipe 53 functions also as the expiratory pathway.

The expiratory valve 51, having a configuration similar to the expiratory valve 15 shown in FIGS. 2A to 2D, is provided on an inner surface 53*f* such that a deformation direction thereof, i.e., a thickness direction thereof, extends along the inner surface 53*f* of the exhaust pipe 53 and a side surface thereof slides along the inner surface 53*f* by the deformation thereof. Thus, the expiratory valve 51 can be transitioned by the deformation of the piezo element between a state in which the vent hole 53*a* is opened and a state in which the vent hole 53*a* is blocked. Moreover, the safety members 52 are formed so as to protrude from an outer surface 53*g* of the exhaust pipe 53 and arranged so as to be dotted near the vent hole 53*a*. It is preferable that the exhaust pipe 53 be set as short as possible within a range not causing a slow responsiveness of the expiratory valve 51 to the expiratory operation. Specifically, a length of the exhaust pipe 53 is preferably within 500 mm, and more preferably within 300 mm.

Figure 8:
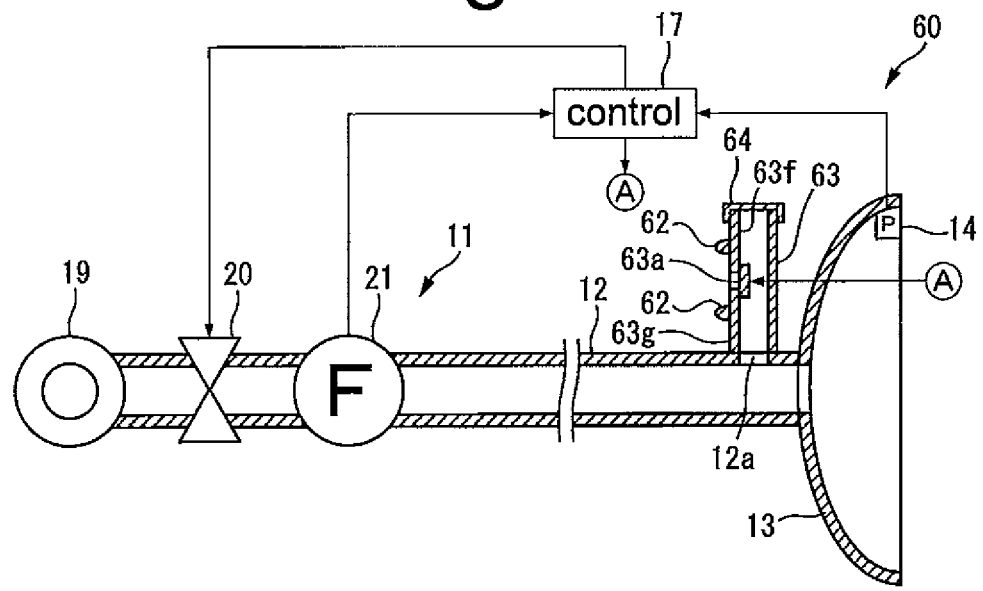
FIG. 8 is a schematic view illustrating a configuration of a respiratory assistance device according to a fourth embodiment of the present invention.

FIG. 8 illustrates, as an example, a configuration of a respiratory assistance device 60 according to the fourth embodiment. In the respiratory assistance device 60, an expiratory valve 61 and a plurality of safety members 62 are provided in the inspiratory pipe 12 via an exhaust pipe 63 instead of providing the expiratory valve 15 and the plurality of safety members 16 directly on the mask 13. More specifically, the exhaust pipe 63 is provided on the inspiratory pipe 12 so that a base end thereof covers the vent hole 12*a*. A tip of the exhaust pipe 63 is closed by a cap 64. Also, a vent hole 63*a* is formed in a middle portion of the exhaust pipe 63. Thus, the inspiratory pipe 12 functions also as the expiratory pathway.

The expiratory valve 61, having a configuration similar to the expiratory valve 15 shown in FIGS. 2A to 2D, is provided on an inner surface 63*f* so that a deformation direction thereof, i.e., a thickness direction thereof, extends along the inner surface 63*f* of the exhaust pipe 63 and a side surface thereof slides along the inner surface 63*f* by the deformation thereof. Thus, the expiratory valve 61 can be transitioned by the deformation of the piezo element between a state in which the vent hole 63*a* is opened and a state in which the vent hole 63*a* is blocked. Moreover, the safety members 62 are formed so as to protrude from an outer surface 63*g* of the exhaust pipe 63 and arranged so as to be dotted near the vent hole 63*a*.

It is preferable that the exhaust pipe 63 be set as short as possible within a range not causing a slow responsiveness of the expiratory valve 61 to the expiratory operation. Specifically, a length of the exhaust pipe 63 is preferably within 500 mm, and more preferably within 300 mm. Moreover, it is preferable that the exhaust pipe 63 be provided at a position as close as possible to the mask 13. Specifically, the exhaust pipe 63 is provided preferably at a position where a length from the mask 13 in the inspiratory pipe 12 is within 150 mm, and more preferably at a position within 50 mm. In other words, the exhaust pipe 63 is provided preferably at a position where a distance of the expiratory pathway from an entrance into a body such as a mouth is within 160 mm, and more preferably at a position within 60 mm.

Figure 9:
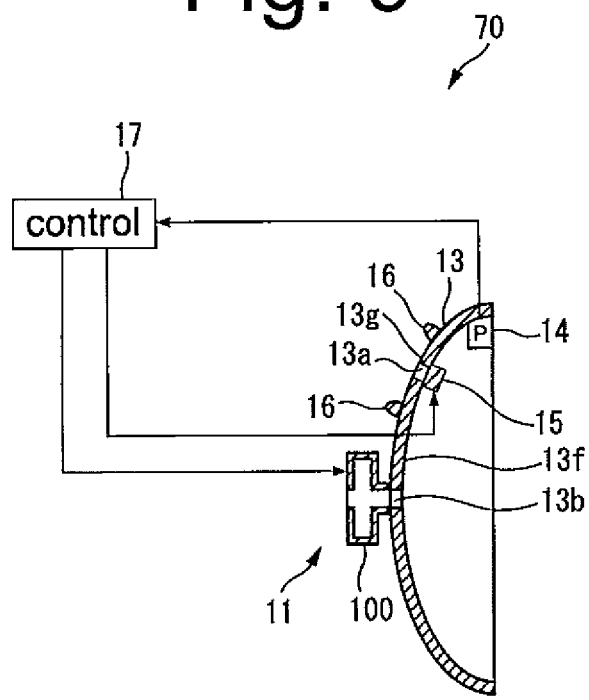
FIG. 9 is a schematic view illustrating a configuration of a respiratory assistance device according to a fifth embodiment of the present invention.
Figure 10:
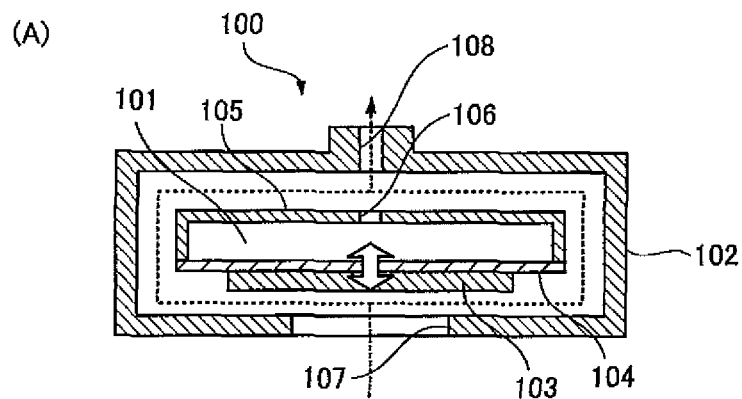
FIG. 10(A) is a cross-sectional view illustrating a configuration example of a micro pump and FIG. 10(B) is a graph showing pressure-flow rate lines of the micro pump.
Figure 10:
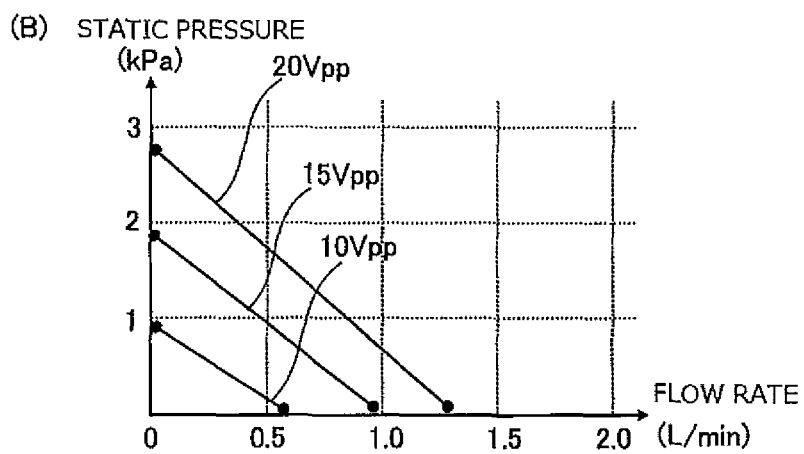

FIG. 9 illustrates, as an example, a configuration of a respiratory assistance device 70 according to the fifth embodiment. The respiratory assistance device 70 includes a micro pump 100 as the supply source 11 and includes only the mask 13 as the inspiratory pathway. In other words, the micro pump 100 is directly connected to the mask 13. This micro pump 100 is the micro pump proposed in Patent Literature WO 2008/069266. As shown in FIG. 10(A), the micro pump 100 includes: a primary blower chamber 101; and a secondary blower chamber 102 formed outside the primary blower chamber 101.

The primary blower chamber 101 includes: a piezoelectric element 103 serving as an oscillation source; a diaphragm 104 to which the piezoelectric element 103 is fixed; and an oscillation frame 105 to form a space together with the diaphragm 104. The oscillation frame 105 has an opening 106 through which a fluid is moved between the inside and outside of the primary blower chamber 101. The secondary blower chamber 102 includes: a suction port 107 on the diaphragm 104 side; and a discharge port 108 provided so as to face the opening 106.

According to the thus described micro pump 100, when the diaphragm 104 resonates by the piezoelectric element 103, the fluid is moved between the primary blower chamber 101 and the secondary blower chamber 102. A fluid resistance due to such a fluid movement causes the oscillation frame 105 to resonate. The resonance of the diaphragm 104 and the oscillation frame 105 causes the fluid to be sucked in from the suction port 107 and to be discharged from the discharge port 108.

The micro pump 100 is suitable for use as a blower for transporting a gas. The micro pump 100 can perform such transportation without employing a check valve. While the micro pump 100 is extremely small, having a box shape with an outer diameter of about 20 mm×20 mm×2 mm, the micro pump 100 can transport air of about 1 L/min at a maximum (when the static pressure is 0 Pa) and can obtain a static pressure of about 2 kPa at a maximum (flow rate of 0 L/min) when the input sine wave is set at 26 kHz under 15 Vpp (Volt peak to peak).

On the other hand, the micro pump 100 transports a fluid by means of the oscillation of the diaphragm 104 caused by the piezoelectric element 103. Thus, there is naturally a limit in its transportable fluid volume. This static pressure-flow rate characteristic also exhibits a straight line as shown in FIG. 10(B). More specifically, in order to obtain a static pressure of about 1 kPa, for example, the flow rate is 0.5 L/min.

If the Vpp of the input sine wave is changed to 10 or 20, the amplitude of the piezoelectric element 103 is thereby changed. Thus, the flow rate and the pressure can be changed. More specifically, if the Vpp of the input sine wave is smoothly changed, the flow rate and the pressure can be smoothly changed. Alternatively, if the frequency of the input sine wave is changed, the flow rate and the pressure can be changed. More specifically, if the frequency of the input sine wave is smoothly changed, the flow rate and the pressure can be smoothly changed. Note however that the flow rate and the pressure each have an upper limit depending on the capacity of the piezoelectric element 103 and the strength or durability of the components. The micro pump 100 is generally used at a rated Vpp and a rated frequency.

Although a monomorph (unimorph) structure in which the single piezoelectric element 103 is attached to the diaphragm 104 is introduced here, it is apparent that a bimorph structure in which two piezoelectric elements are attached together in order to increase the amount of oscillation can be employed instead.

Figure 11:
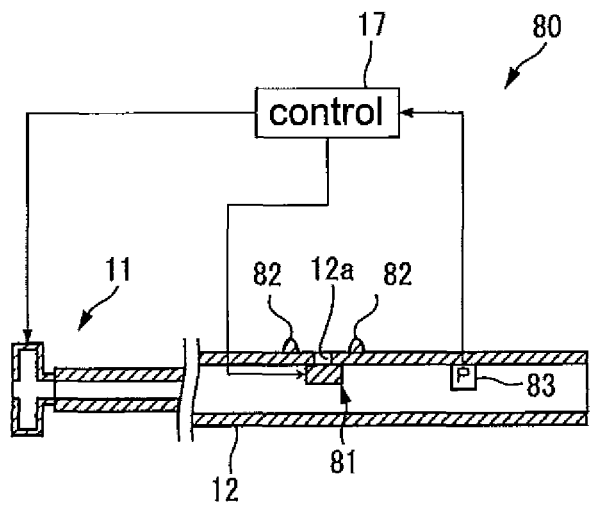
FIG. 11 is a schematic view illustrating a configuration of a respiratory assistance device according to a sixth embodiment of the present invention.

FIG. 11 illustrates, as an example, a configuration of a respiratory assistance device 80 according to the sixth embodiment. The respiratory assistance device 80 includes the micro pump 100 as the supply source 11 and includes only the inspiratory pipe 12 as the inspiratory pathway. In the respiratory assistance device 80, an expiratory valve 81 and a plurality of safety members 82 are provided in the inspiratory pipe 12 instead of providing the expiratory valve 15 and the plurality of safety members 16 in the mask 13. Thus, the inspiratory pipe 12 functions also as the expiratory pathway. It is preferable that the expiratory valve 81 provided at a position as close as possible to the tip of the inspiratory pipe 12 within a range not causing a slow responsiveness to the expiratory operation and within a range not resulting in an insertion thereof into the mouth of a patient. Furthermore, in the respiratory assistance device 80, an air gauge 83 is provided inside the inspiratory pipe 12 instead of providing the air gauge 14 inside the mask 13.

It is apparent that the respiratory assistance device according to the present invention is not limited to the above-described embodiments and various modifications can be made thereto without departing from the scope of the present invention. Also, the constituent elements of the above-described embodiments may be applied to other embodiments to the extent possible.

In other words, in the above-described embodiments, the positions, sizes, shapes, and quantities in the respective configurations can be changed appropriately. Modifications of the first embodiment will be described below as examples.

Figure 12:
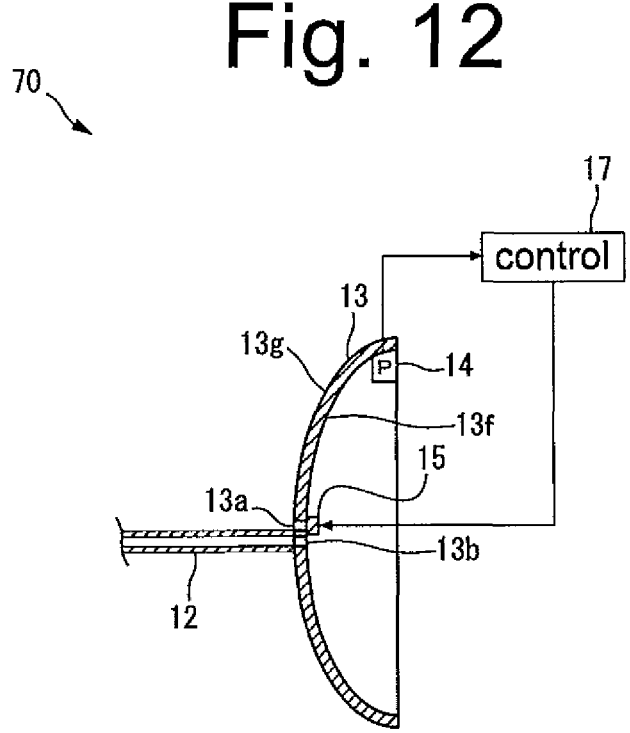
FIG. 12 is a schematic view illustrating an expiratory valve capable of selectively blocking an expiratory hole and an inspiratory hole provided in a mask.
Figure 13:
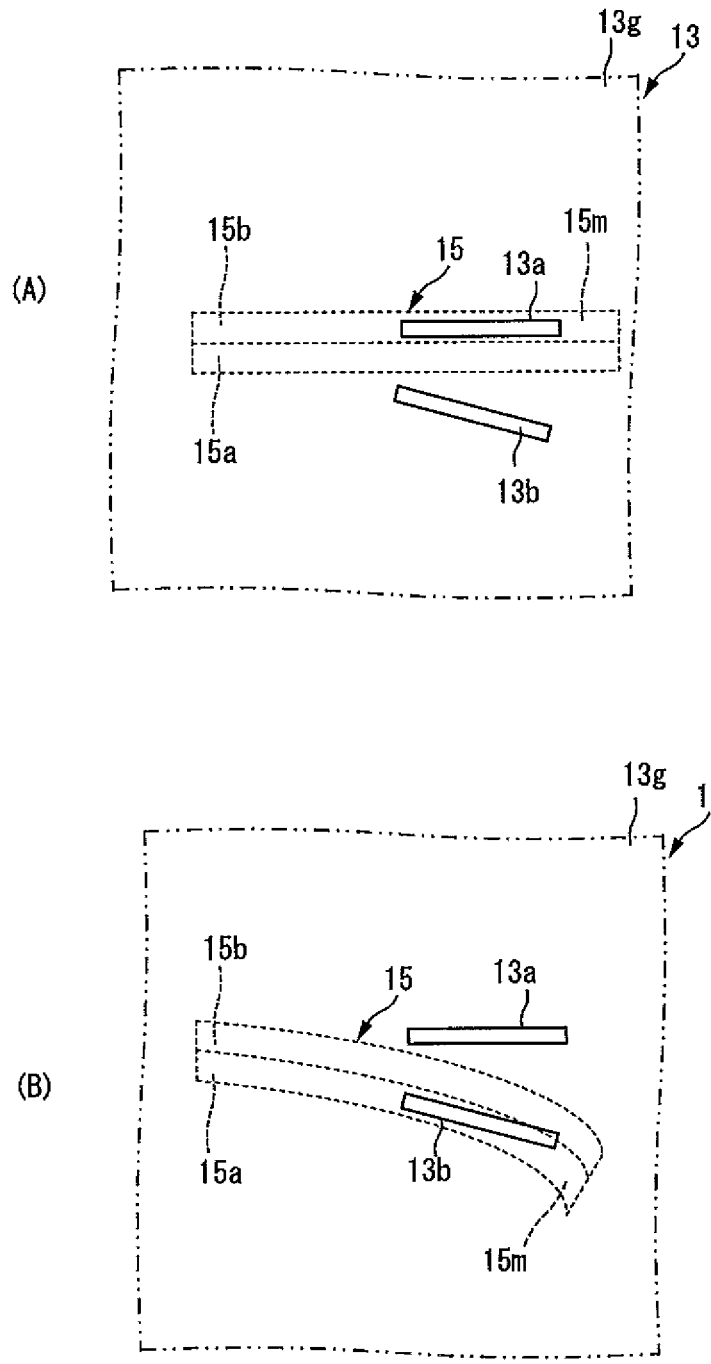
FIG. 13 shows schematic views illustrating the expiratory valve capable of selectively blocking the expiratory hole and the inspiratory hole provided in the mask wherein (A) shows a state in which the expiratory valve blocks only the expiratory hole and (B) shows a state in which the expiratory valve blocks only the inspiratory hole.

Modifications of the first embodiment will be described specifically as examples. As shown in FIGS. 12 and 13, it is preferable that the expiratory hole 13a and the inspiratory hole 13b formed in the mask 13 be provided so as to be close to each other. "Being close" herein refers to a range smaller than the deformation amount of the piezo element 15a. Thus, the expiratory valve 15 can be transitioned by the deformation of the piezo element 15a between a state in which only the expiratory hole 13a formed in the mask 13 is blocked (see FIG. 13(A)) and a state in which only the inspiratory hole 13b is blocked (see FIG. 13(B)). This reliably allows for switching between a state in which the expiratory air inside the mask 13 is emitted to the outside of the mask 13 and a state in which the inspiratory gas from the inspiratory pipe 12 is sent into the mask 13. Furthermore, since the inspiratory pipe 12 is formed in a protruding manner near the expiratory hole 13a on the outer surface of the mask 13, the inspiratory pipe 12 functions also as a safety member.

Figure 14:
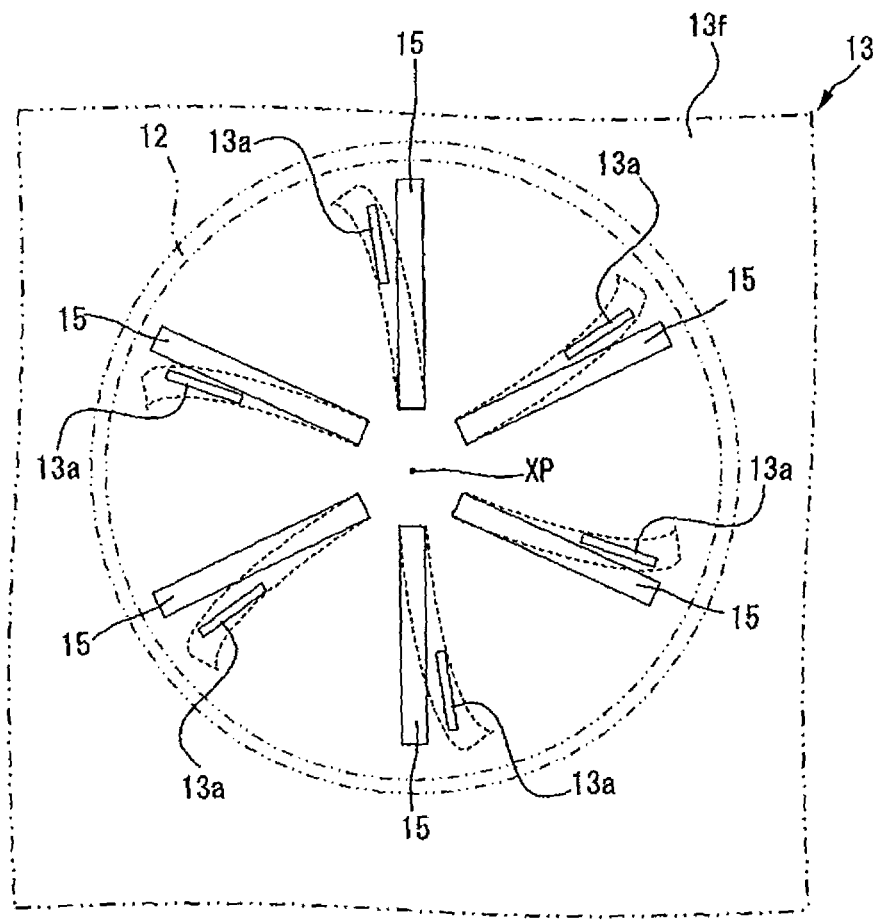
FIG. 14 is a schematic view of a mask having a plurality of expiratory holes.

Alternatively, as shown in FIG. 14, a plurality of expiratory holes 13a may be provided in the mask 13. These expiratory holes 13a are provided at portions of the mask 13 facing the aperture plane of the tip portion of the inspiratory pipe 12. Alternatively, any reference position XP may be set at a portion of the mask 13 facing the aperture plane of the tip portion of the inspiratory pipe 12 and the expiratory holes 13a may be arranged around the reference position XP. It is preferable that an expiratory valve 15 be provided for each of the expiratory holes 13a formed in the mask 13 to open and close the corresponding expiratory hole 13a. The plurality of expiratory valves 15 are controlled independently of one another to open and close the expiratory holes 13a, respectively. Thus, by changing the number of the expiratory valves 15 to be opened, the flow rate of the expiratory air can be adjusted. In this manner, without controlling the applied amount of a voltage to the piezo element 15a, the flow rate of the expiratory air can be adjusted stepwisely only by controlling ON and OFF of the voltage to the piezo elements 15a in order to change the number of the expiratory valves 15 to be opened. In other words, the flow rate of the expiratory air can be adjusted with such a simple control. Moreover, the flow rate of the expiratory air can be adjusted more smoothly by controlling the applied amount of the voltage to the piezo element 15a.

In the above-described embodiment, the expiratory valve 15 having the piezo element 15a, which is a deformable member, is used as the opening and closing mechanism. Also, the expiratory valve 15 is configured so as to be transitioned by the deformation of the piezo element 15a between the state in which the expiratory hole 13a is blocked by the side surface 15m (see FIG. 1) of the expiratory valve 15 (see FIGS. 2C and 2D) and the state in which the expiratory hole 13a is opened (see FIGS. 2A and 2B). However, the present invention is not limited thereto. The expiratory hole 13a may be opened and closed by using a cover 85 provided at a free end side of the expiratory valve 15. In this case, the expiratory valve 15 and the cover 85 together form the opening and closing mechanism (see FIG. 15). The cover 85 has a sliding surface to slide along the inner surface 13f. The cover 85 is disposed so that the deformation direction of the expiratory valve 15, i.e., the thickness direction of the expiratory valve 15, extends along the inner surface 13f of the mask 13 and the sliding surface slides along the inner surface 13f by the deformation of the expiratory valve 15.

Alternatively, in the above-described first to fourth embodiments, the micro pump 100 may be provided as the supply source 11 in place of the gas tank 19 or the like. In each of the above-described embodiments including the cases of the above-described fifth and sixth embodiments, a plurality of micro pumps 100 may be provided and disposed in series or in parallel or disposed in a matrix.

Alternatively, while a mask 13 covering a mouth and a nose is provided as the inspiratory pathway and the expiratory pathway in the above-described first to fifth embodiments, a wearing device such as a nosepiece worn by a nose may be provided in place of the mask 13.

Note that the shape of the expiratory hole 13a or the inspiratory hole 13b (see FIG. 14) such as a circle (see FIG. 15), an ellipse, a polygon, or a slit shape (see FIGS. 2A to 2D) may be appropriately determined depending on its usage.

When the hole is opened and closed by means of a temperature change, a bimetal may be used as the opening and closing mechanism. In this case, it is advantageous in that there is no need for a control unit controller. Coefficients of thermal expansion, shapes, and sizes of the materials of the bimetal may be determined so as to achieve transition between the opened state and the closed state.

Figure 2A:
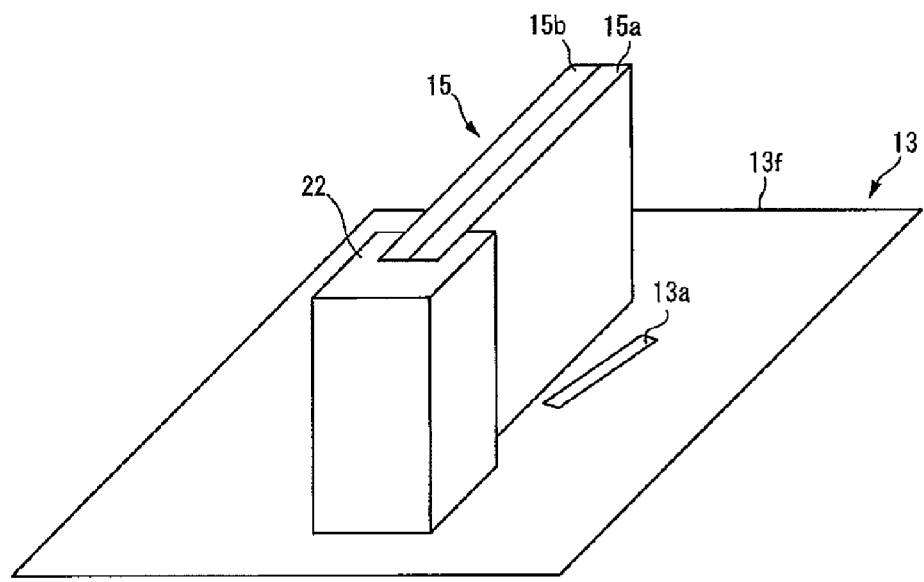
FIG. 2A is a schematic view of an expiratory valve provided in a mask, illustrating a state in which the expiratory valve opens an expiratory hole.
Figure 2B:
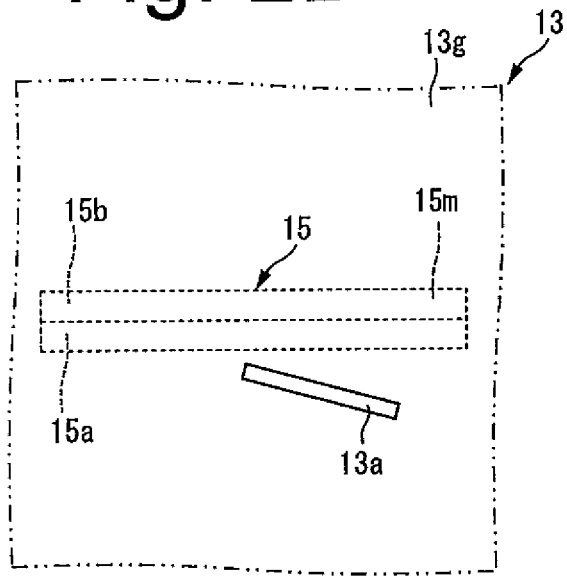
FIG. 2B is a schematic view of the expiratory valve provided in the mask, illustrating the state in which the expiratory valve opens the expiratory hole.
Figure 2C:
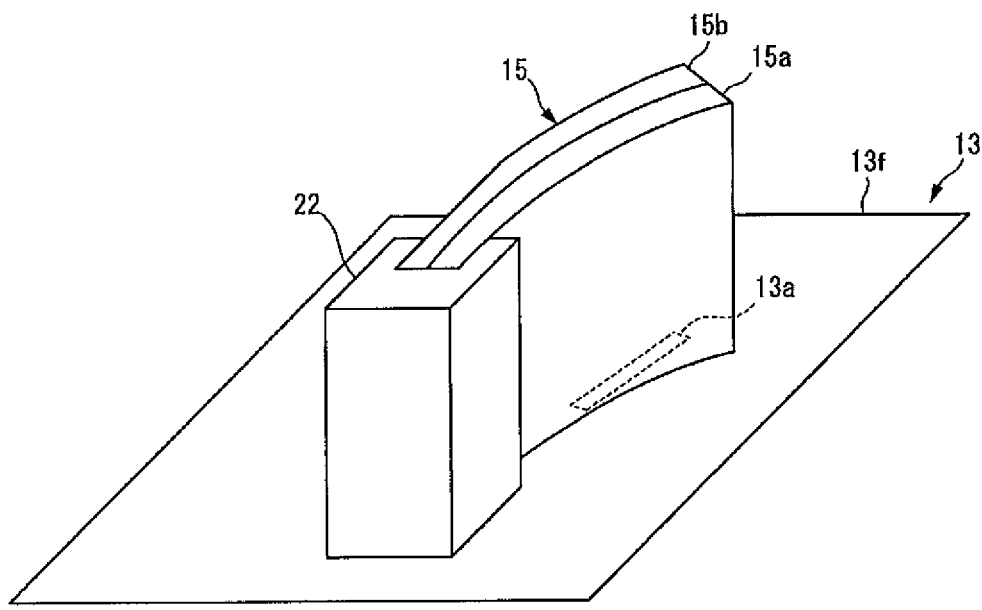
FIG. 2C is a schematic view of the expiratory valve provided in the mask, illustrating a state in which the expiratory valve blocks the expiratory hole.
Figure 2D:
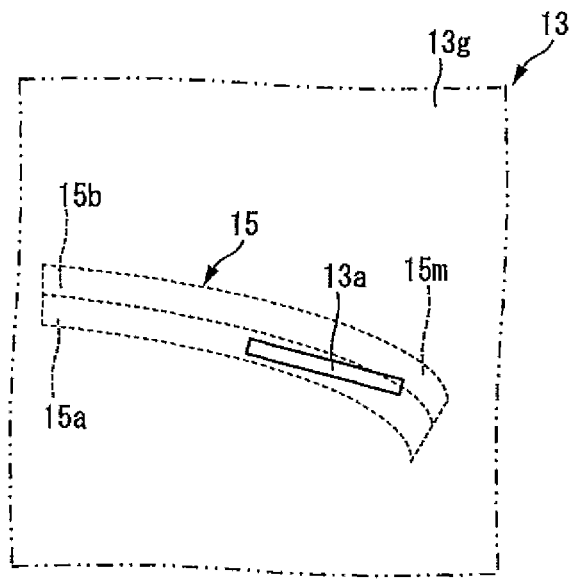
FIG. 2D is a schematic view of the expiratory valve provided in the mask, illustrating the state in which the expiratory valve blocks the expiratory hole.

In the above-described embodiments, the expiratory valve is deformed between the fully-opened state of the expiratory hole 13a (see FIGS. 2A and 2B) and the fully-closed state of the expiratory hole 13a (see FIGS. 2C and 2D). Depending on its usage, however, the expiratory valve 15 may be deformed between a state in which the opening amount of the expiratory hole 13a is A and a state in which the opening amount of the expiratory hole 13a is B which is greater than A. This allows the flow rate of the expiratory air to be adjusted stepwisely.

Moreover, the above-described opening and closing device can be applied not only to the opening and closing of a hole through which the expiratory air passes but also to the opening and closing of a hole through which a fluid (a gas or a liquid) passes and the opening and closing of a hole through which a solid passes.

Figure 16:
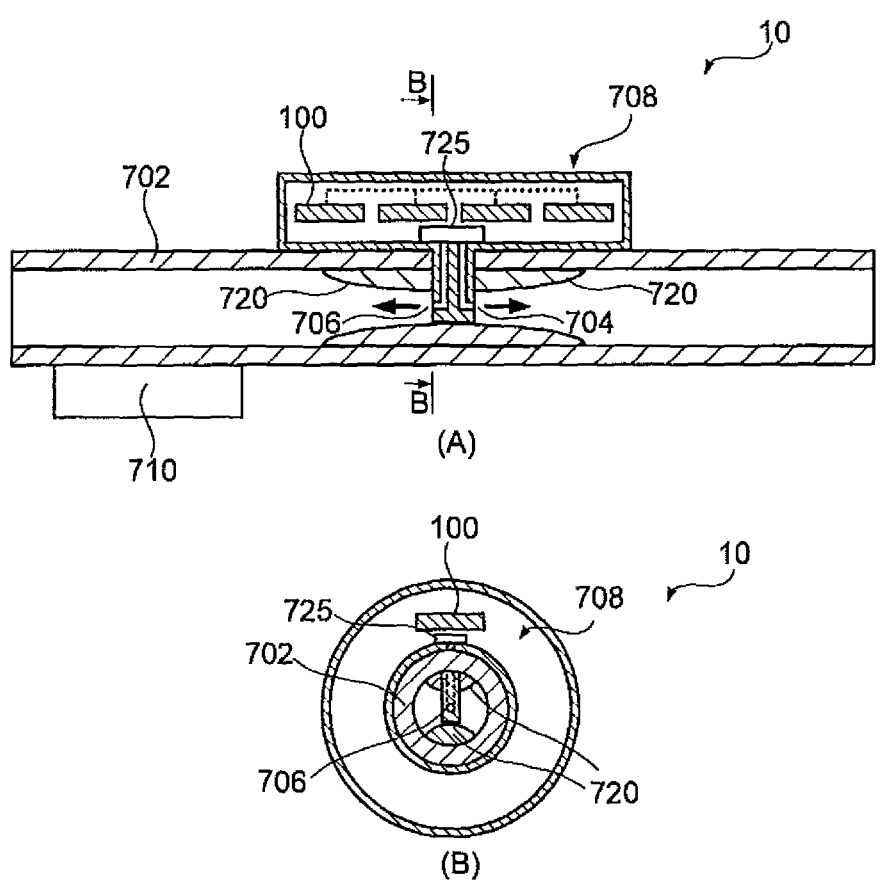
FIG. 16 shows schematic views illustrating a respiratory assistance device including an expiration and inspiration switching valve capable of selectively blocking an expiratory nozzle and an inspiratory nozzle.

Furthermore, another embodiment will be described. A respiratory assistance device 10 shown in FIG. 16 is configured to include: a flow passage 702 through which a gas for respiration passes; an expiratory nozzle 704 and an inspiratory nozzle 706 disposed in the flow passage 702 and capable of emitting acceleration air in an expiratory direction and in an inspiratory direction, respectively; a pump unit 708 disposed on an outer surface of the flow passage 702 in a circumferential direction thereof; and a battery 710 for driving the pump unit 708. Venturi walls 720 are disposed near the expiratory and inspiratory nozzles 704 and 706 disposed in the flow passage 702. The Venturi wall 720 includes a portion extending from the inspiratory nozzle 706 toward the inspiratory direction and a portion extending from the expiratory nozzle 704 toward the expiratory direction. Note that the battery 710 may be disposed at a remote location or may be omitted by connecting a power supply line.

Figure 17:
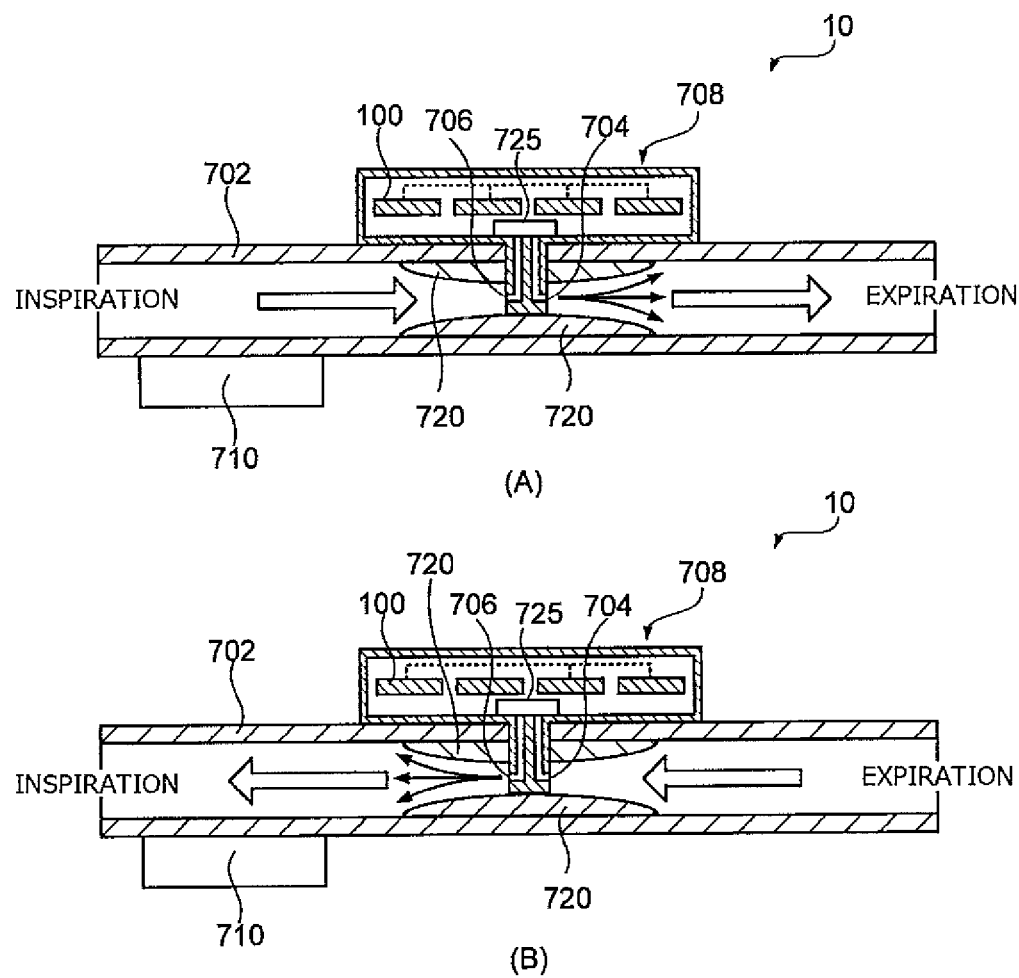
FIG. 17(A) is a schematic view of the respiratory assistance device when air is emitted from the expiratory nozzle and FIG. 17(B) is a schematic view of the respiratory assistance device when air is emitted from the inspiratory nozzle.

In the pump unit 708, a plurality of (for example, four) micro pumps 100 are arranged. The pump unit 708 is provided with an integrated discharge port (not shown) which is a place from which air transported by all the micro pumps 100 is discharged finally. An expiration and inspiration switching valve 725 is disposed at the integrated discharge port. The expiration and inspiration switching valve 725 has a configuration similar to that of the above-described expiratory valve 15. The expiration and inspiration switching valve 725 is switchable between a state in which the inspiratory nozzle 706 is blocked and a state in which the expiratory nozzle 704 is blocked. If the expiration and inspiration switching valve 725 blocks the inspiratory nozzle 706, the air sent out from the pump unit 708 is emitted from the expiratory nozzle 704 as shown in FIG. 17(A). The air emitted from the expiratory nozzle 704 is spread out by the Venturi walls 720, thereby setting the expiratory side in a negative pressure state. Thus, carbon dioxide discharged from the inspiratory side (lung side) is attracted and caused to flow in the expiratory direction. Consequently, the expiratory operation can be assisted. When the expiration and inspiration switching valve 725 blocks the expiratory nozzle 704, on the other hand, the air sent out from the pump unit 708 is emitted from the inspiratory nozzle 706 as shown in FIG. 17(B). The air emitted from the inspiratory nozzle 706 is spread out by the Venturi walls 720, thereby setting the inspiratory side in a negative pressure state. Thus, oxygen supplied from the expiratory side is sucked in and is caused to flow in the inspiratory direction (lung side). Consequently, the inspiratory operation can be assisted.

Furthermore, as a result of the reduced distance between the pump unit 708 and the expiratory and inspiratory nozzles 704 and 706, an improved responsiveness in the breathing assisting operation can be obtained.

In the above-described embodiment, as shown in FIGS. 2A to 2D, an expiratory valve having the monomorph (unimorph) structure formed by the piezo element (piezoelectric element) 15a and the metal plate 15b is employed as the expiratory valve 15 and the piezo element 15a is switched between the extended state (see FIGS. 2A and 2B) and the bent state (see FIGS. 2C and 2D) by turning ON and OFF the voltage application to the piezo element 15a. However, the behavior of the piezo element 15 in the ON and OFF control of the voltage application includes not only deformation in the thickness direction thereof but also deformation in the width direction thereof (the height direction from the inner surface 13f). Therefore, if the turning ON and OFF of the voltage application to the piezo element 15a is repeatedly performed, a gap is created between the expiratory valve 15 and the inner surface 13f as a result of the deformation in the width direction of the piezo element 15a. Consequently, the expiratory valve 15 can no longer close the expiratory hole 13a.

Figure 18:
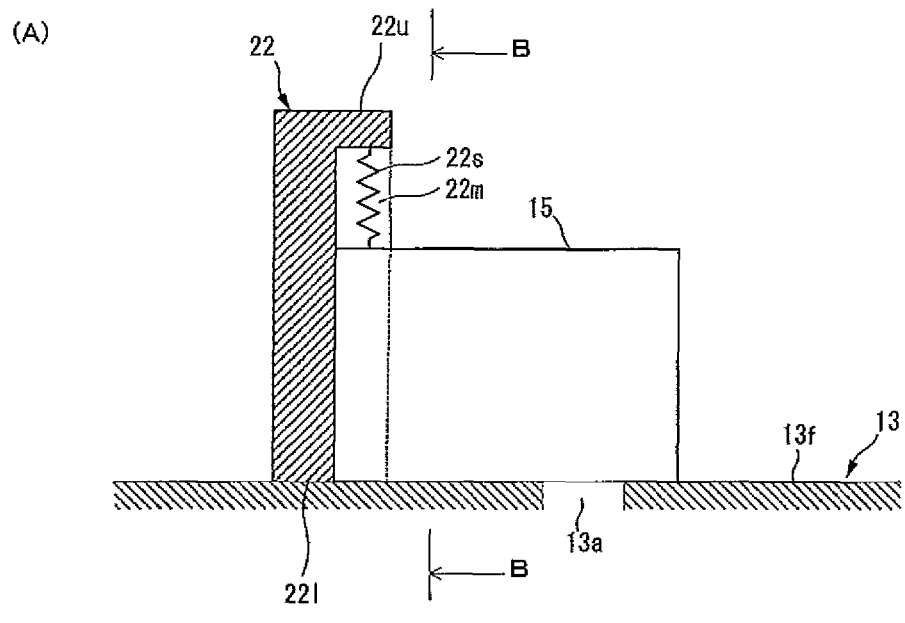
FIG. 18(A) is a cross-sectional view taken along the line A-A, illustrating an outline of an expiratory valve provided in a mask and components disposed therearound.
FIG. 18(B) is a cross-sectional view taken along the line B-B, illustrating an outline of the expiratory valve provided in the mask and the components disposed therearound.
Figure 18:
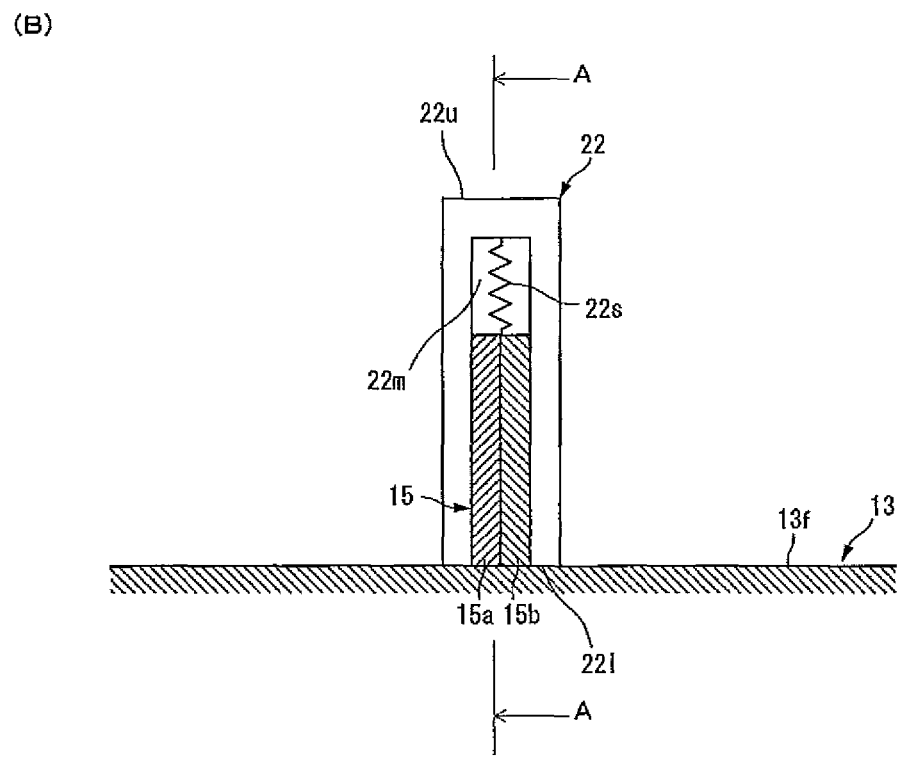
Figure 19:
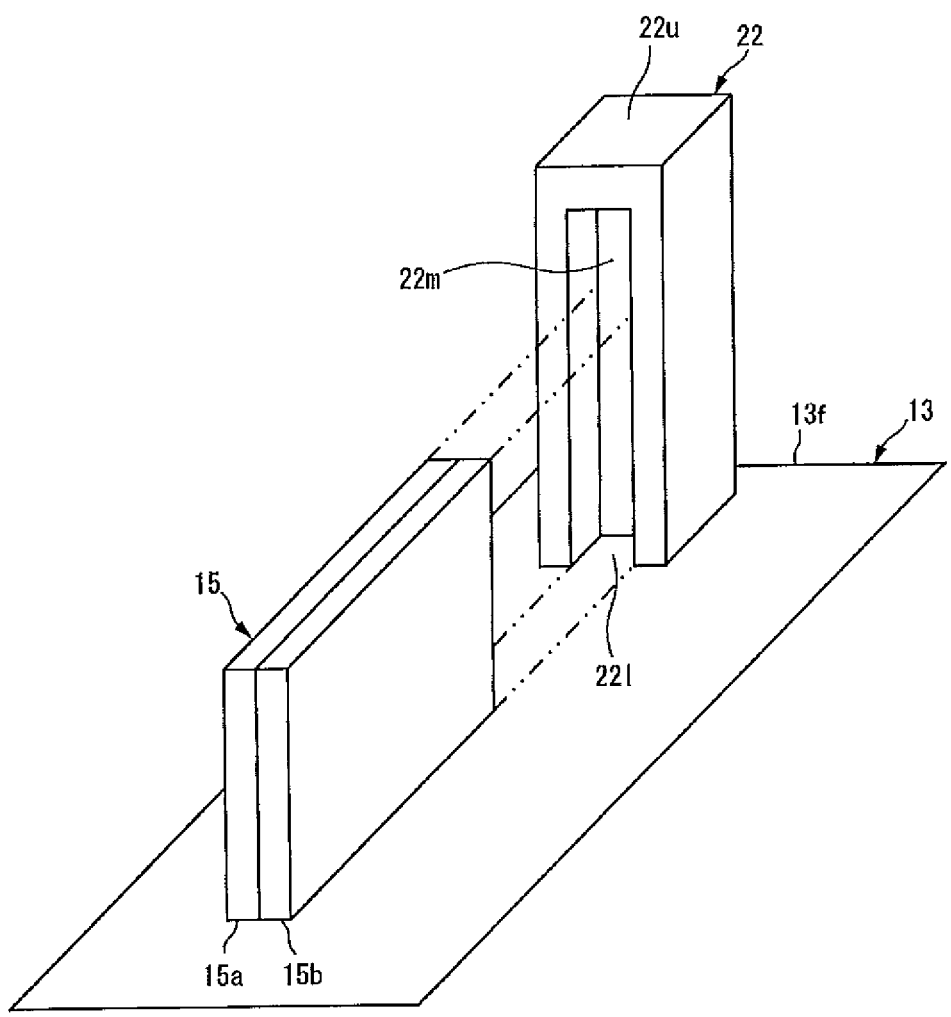
FIG. 19 is an exploded perspective view illustrating an outline of the expiratory valve provided in the mask and the respective components disposed around the expiratory valve.

If such is the case, it is preferable that a holding groove 22m capable of holding one end of the expiratory valve 15 be formed in the fixing member 22 and a spring 22s for biasing the expiratory valve 15 toward the inner surface 13f be disposed in the holding groove 22m as shown in FIGS. 18 to 19.

The holding groove 22m is formed on a side surface of the fixing member 22 with a size into which the one end of the expiratory valve 15 can be inserted. The holding groove 22m extends in the height direction from the inner surface 13f (the width direction of the expiratory valve 15). Moreover, the dimension of the holding groove 22m in the width direction of the expiratory valve 15 is longer than that of the expiratory valve 15. Furthermore, one end side of the holding groove 22m, i.e., an upper surface (the surface opposite to a lower surface) 22u side of the fixing member 22, is closed whereas the other end side thereof, i.e., a lower surface (the surface in contact with the inner surface 13f) 22l side of the fixing member 22, is opened at the lower surface 22l.

The spring 22s is disposed in the holding groove 22m over a range from the one end of the expiratory valve 15 toward the upper surface 22u. One end of the spring 22s abuts against the surface of the holding groove 22m on the upper surface 22u side. The other end of the spring 22s abuts against the surface of the expiratory valve 15 on the upper surface 22u side. Therefore, the spring 22s biases the expiratory valve 15 downward, i.e., toward the inner surface 13f.

In this manner, the spring 22s biasing the expiratory valve 15 toward the inner surface 13f is disposed. Thus, even when the deformation of the piezo element 15a is repeatedly performed, a gap is less likely to be formed between the expiratory valve 15 and the inner surface 13f. Consequently, the closing operation of the expiratory hole 13a by the expiratory valve 15 can be reliably performed.

Figure 15:
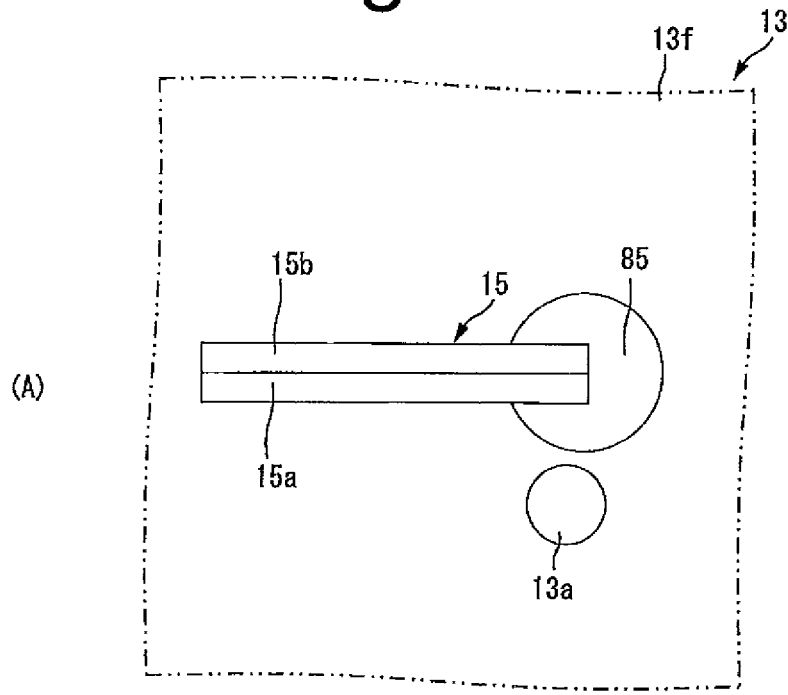
FIG. 15 shows schematic views of an expiratory valve including a piezo element and a cover provided in the piezo element and capable of opening and closing an expiratory hole by deformation of the piezo element.
Figure 15:
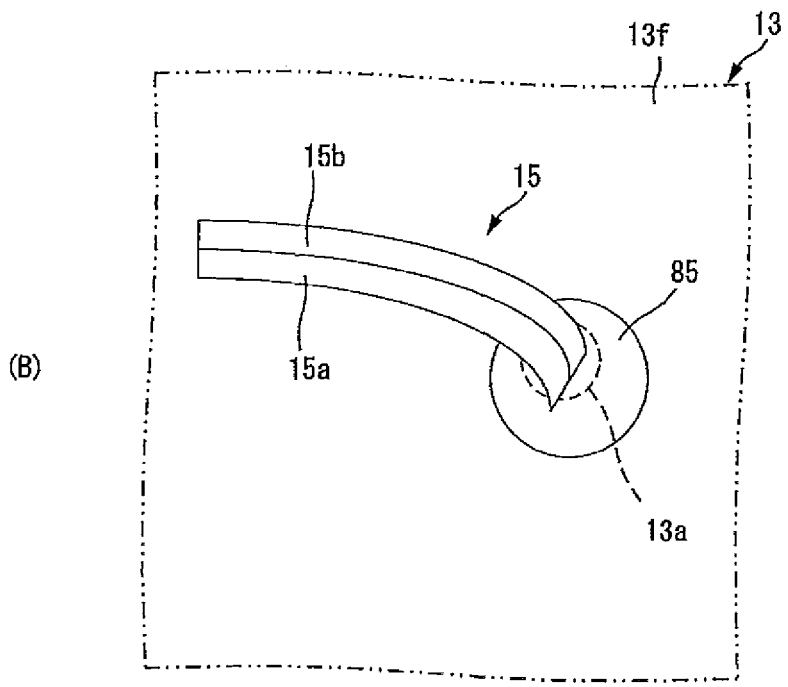

Alternatively, if the expiratory hole 13a is opened and closed by the cover 85 provided at the free end side of the expiratory valve 15 as shown in FIG. 15, a spring for biasing the cover 85 toward the inner surface 13f may be provided between the free end of the expiratory valve 15 and the cover 85.

The invention claimed is:

1. An opening and closing device comprising:
    a separating member having a separating surface with a hole provided therein through which a fluid can pass when opened; and
    an opening and closing mechanism having a plate-shaped deformable member comprising a piezoelectric element and which is oriented such that its thickness direction always extends along the separating surface and deforms in its thickness direction along a plane direction that extends along the separating surface, wherein
    the opening and closing mechanism is transitioned by deformation of the deformable member along the separating surface between first and second states in which opening amounts of the hole differ from each other.

2. The opening and closing device according to claim 1, wherein
    the hole is formed in a slit shape, and
    the deformable member covers the hole with a side surface thereof.

3. The opening and closing device according to claim 1, wherein
    the opening and closing mechanism includes a cover provided at a free end side of the deformable member, and covers the hole by moving the cover.

4. The opening and closing device according to claim 1, wherein
    said hole includes a first hole and a second hole and the first hole and the second hole are opened in the separating surface,
    the opening and closing mechanism can be transitioned by deforming the common deformable member between two states, and
    an opening amount of the first hole in one state of the two states is different from an opening amount of the first hole in the other state, and an opening amount of the second hole in the one state of the two states is different from an opening amount of the second hole in the other state.

5. The opening and closing device according to claim 1, wherein the deformable member is a piezoelectric element, and
    the opening and closing device comprises a controller for controlling deformation of the piezoelectric element.

6. The opening and closing device according to claim 1, comprising a biasing mechanism for biasing the opening and closing mechanism toward the separating surface.

7. A respiratory assistance device comprising the opening and closing device according to claim 1, wherein
    the separating member is formed by: a mask for covering a nose or a mouth; and a communicating pipe communicated with a space formed inside the mask in a worn state.

8. The respiratory assistance device according to claim 7, wherein the mask includes the separating member so that the hole is formed in the mask.

9. The respiratory assistance device according to claim 7, wherein the communicating pipe includes the separating member so that the hole is formed in the communicating pipe.

10. The respiratory assistance device according to claim 7, wherein the hole forms an expiratory pathway through which expiratory air exhaled from the nose or the mouth passes.

11. A respiratory assistance device comprising:
    the opening and closing device according to claim 1;
    a flow passage through which an expiratory or inspiratory gas passes;
    an inspiratory nozzle disposed in the flow passage, for jetting an acceleration gas in an inspiratory direction;
    an expiratory nozzle disposed in the flow passage closer to an expiratory direction side than the inspiratory nozzle, for jetting an acceleration gas in the expiratory direction;
    a pump unit for supplying the acceleration gas to the inspiratory nozzle and the expiratory nozzle;
    an inspiratory Venturi wall extending from the inspiratory nozzle toward the inspiratory direction in the flow passage so as to spread out the acceleration gas emitted from the inspiratory nozzle in order to set the inspiratory direction side from the inspiratory nozzle at a negative pressure; and
    an expiratory Venturi wall extending from the expiratory nozzle toward the expiratory direction in the flow passage so as to spread out the acceleration gas emitted from the expiratory nozzle in order to set the expiratory direction side from the expiratory nozzle at a negative pressure, wherein
    the opening and closing device can be transitioned between a state in which one of the inspiratory nozzle and the expiratory nozzle is blocked and a state in which the other one of them is blocked.

* * * * *